(12) United States Patent
Roche

(10) Patent No.: US 11,179,264 B2
(45) Date of Patent: Nov. 23, 2021

(54) PRESSURE ULCER DRESSING ASSEMBLY

(71) Applicant: Frank Roche, Chetek, WI (US)

(72) Inventor: Frank Roche, Chetek, WI (US)

(73) Assignee: The Safety Dressing Company, Chetek, WI (US)

( * ) Notice: Subject to any disclaimer, the term of this patent is extended or adjusted under 35 U.S.C. 154(b) by 312 days.

(21) Appl. No.: 16/551,148

(22) Filed: Aug. 26, 2019

(65) Prior Publication Data

US 2021/0059852 A1    Mar. 4, 2021

(51) Int. Cl.
*A61F 5/34*      (2006.01)
*A61F 5/30*      (2006.01)
*A61F 13/02*     (2006.01)

(52) U.S. Cl.
CPC ............ *A61F 5/30* (2013.01); *A61F 13/0269* (2013.01)

(58) Field of Classification Search
CPC .......... A61F 13/0269; A61F 5/03; A61F 5/30; A61F 5/32; A61F 5/34; A61F 13/063; A61F 13/069; A61F 5/041
USPC ................................................. 128/889–894
See application file for complete search history.

(56) References Cited

U.S. PATENT DOCUMENTS

| | | | | |
|---|---|---|---|---|
| 1,562,454 A | * | 11/1925 | Jenkins | A61F 13/064 |
| | | | | 128/846 |
| 3,556,096 A | | 1/1971 | Fuller | |
| 4,104,746 A | * | 8/1978 | Goetz | A61F 13/069 |
| | | | | 5/650 |
| 4,495,942 A | * | 1/1985 | Palumbo | A61F 13/066 |
| | | | | 602/27 |
| 4,573,456 A | * | 3/1986 | Spann | A61F 13/069 |
| | | | | 602/27 |
| 4,688,562 A | | 8/1987 | Buchan et al. | |
| 4,719,926 A | * | 1/1988 | Nelson | A43B 3/0031 |
| | | | | 36/89 |
| 5,098,421 A | | 3/1992 | Zook | |
| 5,462,519 A | | 10/1995 | Carver | |
| D430,674 S | | 9/2000 | Dunshee | |
| 6,149,613 A | * | 11/2000 | Klein | A61F 5/0195 |
| | | | | 128/882 |

(Continued)

FOREIGN PATENT DOCUMENTS

FR          2746297 A1    9/1997

OTHER PUBLICATIONS

International Search Report and Written Opinion dated Sep. 14, 2020 re PCT/US20/70170 (8 pages).

*Primary Examiner* — Camtu T Nguyen
(74) *Attorney, Agent, or Firm* — PatentXP PLLC; Stephen J. Kontos

(57) ABSTRACT

A pressure ulcer dressing assembly includes a cushion that is hollow. The cushion is curved such that the cushion has a C shape and the cushion is positionable around a pressure ulcer on a patient having the cushion partially encircling the pressure ulcer. A gel fills the cushion and the gel absorbs weight of the patient when the cushion is positioned on the patient. In this way the cushion inhibits the pressure ulcer from is exposed to pressure thereby enhancing healing the pressure ulcer. A dressing is coupled to the cushion, the dressing extends laterally across the cushion and the dressing covers the pressure ulcer when the cushion is positioned on the patient. A pair of adhesive pads is each coupled to the dressing for retaining the dressing and the cushion on the patient.

7 Claims, 6 Drawing Sheets

(56) References Cited

U.S. PATENT DOCUMENTS

| | | | |
|---|---|---|---|
| 6,308,713 B1* | 10/2001 | Coleman | A61F 5/0195 128/882 |
| 6,640,810 B1* | 11/2003 | Callsen | A61F 5/0195 128/882 |
| 7,182,085 B1 | 2/2007 | Larsen | |
| 2001/0051781 A1* | 12/2001 | Augustine | A61F 13/022 602/41 |
| 2002/0007136 A1* | 1/2002 | Narula | A61F 13/069 602/46 |
| 2004/0195898 A1 | 10/2004 | Barrett | |
| 2009/0260639 A1 | 10/2009 | Hsu et al. | |
| 2012/0030878 A1 | 2/2012 | Davenport et al. | |
| 2014/0130261 A1* | 5/2014 | Gumbrecht | A47C 7/383 5/644 |
| 2015/0061346 A1 | 3/2015 | Featherstone | |
| 2016/0184140 A1 | 6/2016 | Hu et al. | |
| 2018/0021177 A1* | 1/2018 | Bedford | A61F 13/00063 602/46 |

* cited by examiner

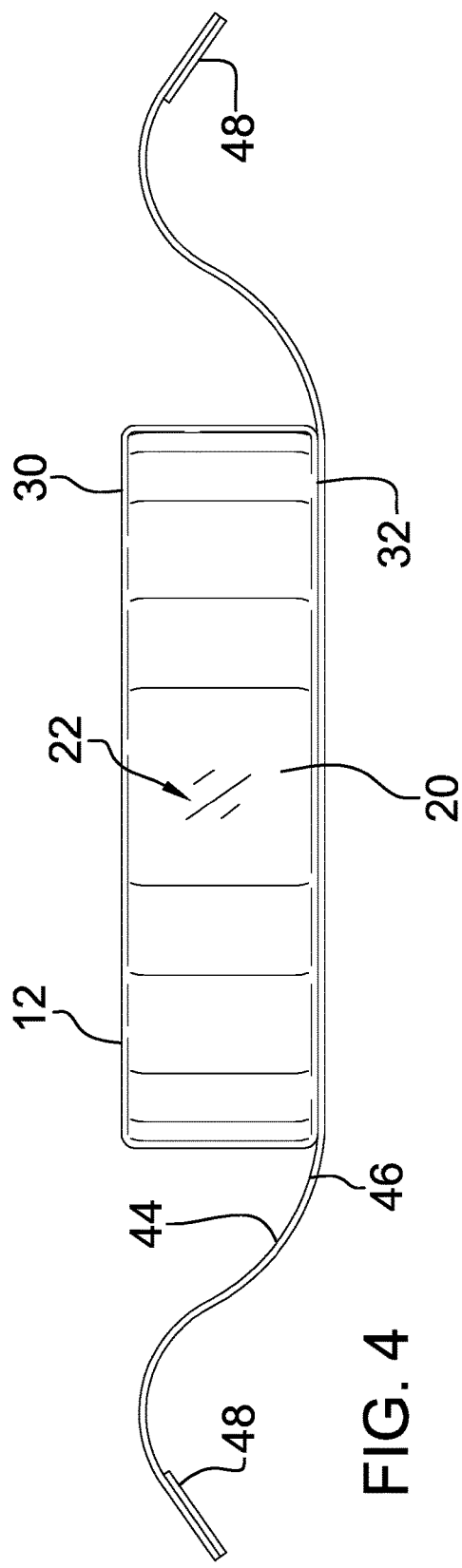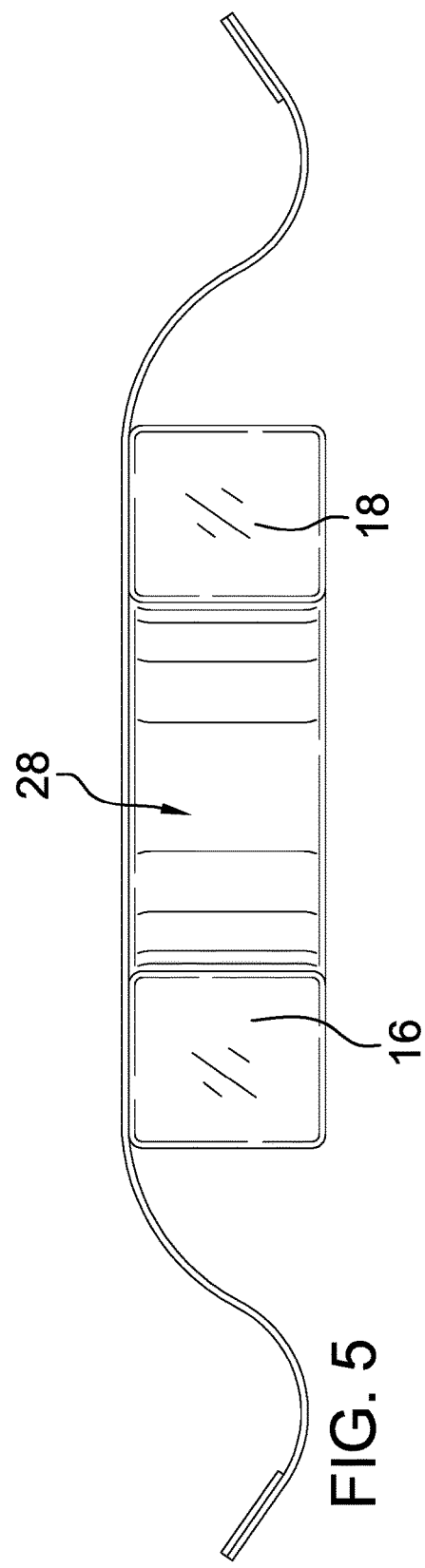

PRESSURE ULCER DRESSING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to dressing devices and more particularly pertains to a new dressing device for inhibiting a pressure ulcer from being exposed to pressure.

(2) Description of Related Art Including Information Disclosed Under 37 CFR 1.97 and 1.98

The prior art relates to dressing devices.

BRIEF SUMMARY OF THE INVENTION

An embodiment of the disclosure meets the needs presented above by generally comprising a cushion that is hollow. The cushion is curved such that the cushion has a C shape and the cushion is positionable around a pressure ulcer on a patient having the cushion partially encircling the pressure ulcer. A gel fills the cushion and the gel absorbs weight of the patient when the cushion is positioned on the patient. In this way the cushion inhibits the pressure ulcer from is exposed to pressure thereby enhancing healing the pressure ulcer. A dressing is coupled to the cushion, the dressing extends laterally across the cushion and the dressing covers the pressure ulcer when the cushion is positioned on the patient. A pair of adhesive pads is each coupled to the dressing for retaining the dressing and the cushion on the patient.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 4 is a back view of an embodiment of the disclosure.

FIG. 5 is a front view of an embodiment of the disclosure.

DETAILED DESCRIPTION OF THE INVENTION

Figure 1:
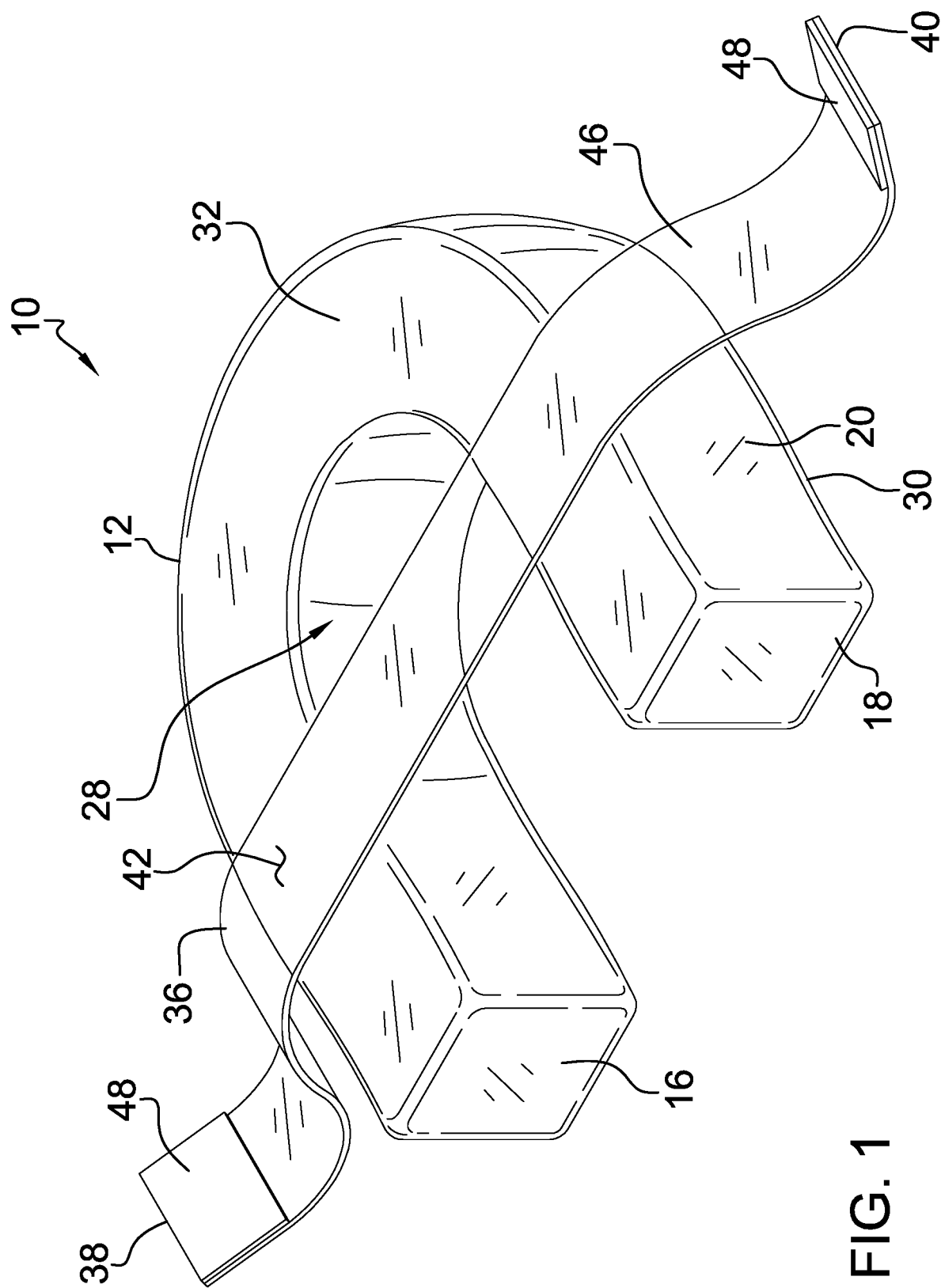
FIG. 1 is a bottom perspective view of a pressure ulcer dressing assembly according to an embodiment of the disclosure.
Figure 2:
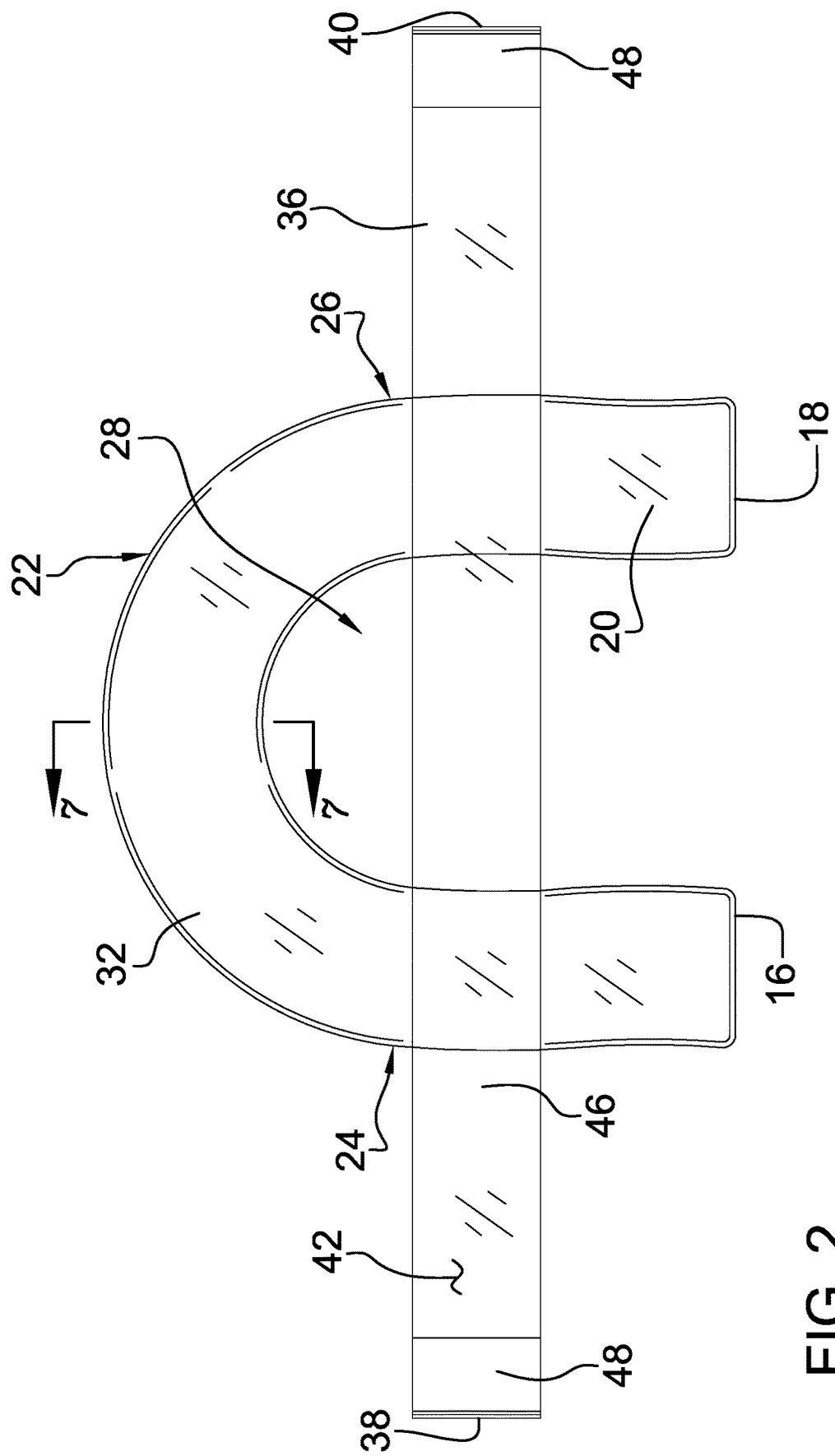
FIG. 2 is a bottom view of an embodiment of the disclosure.
Figure 3:
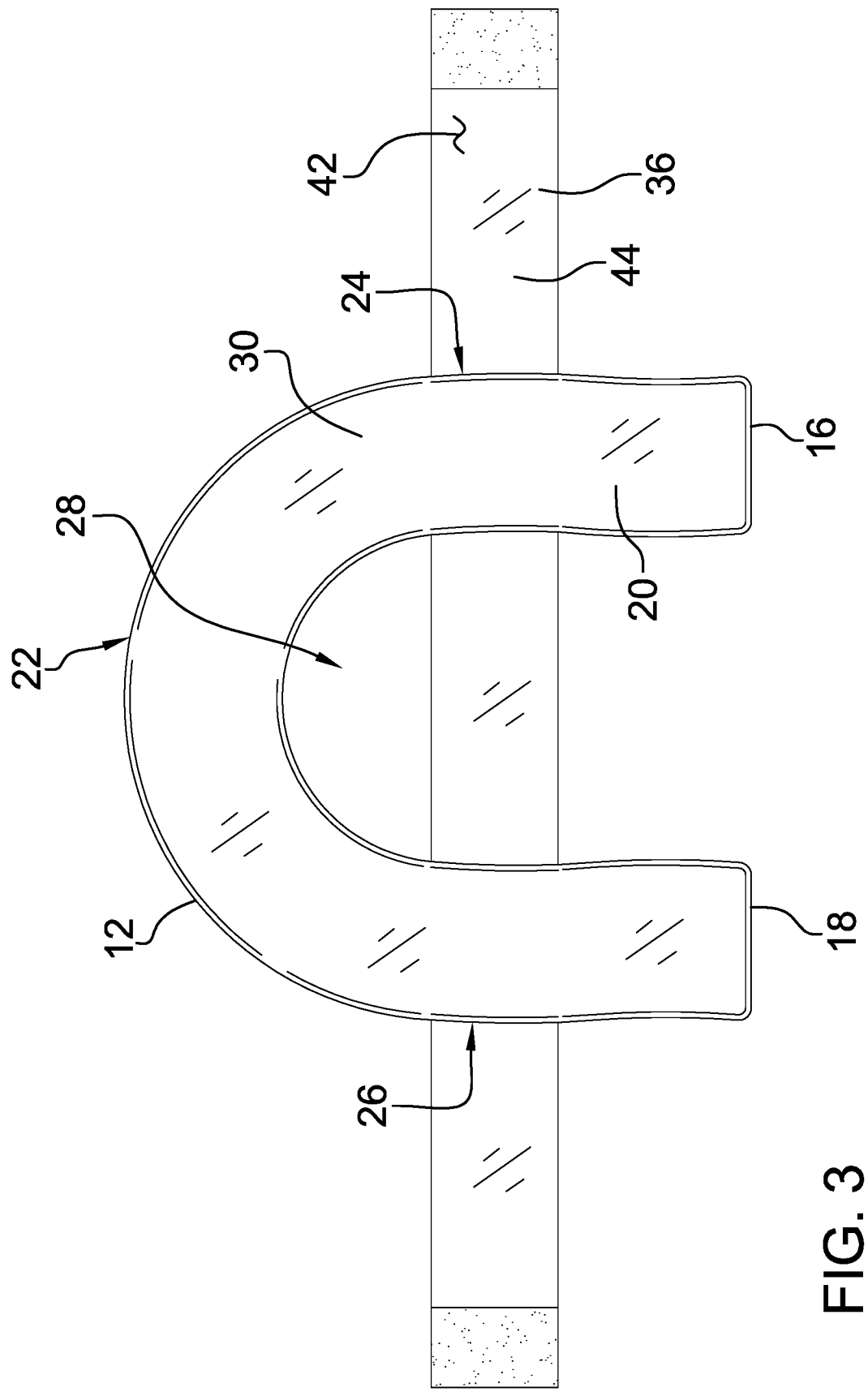
FIG. 3 is a top view of an embodiment of the disclosure.
Figure 6:
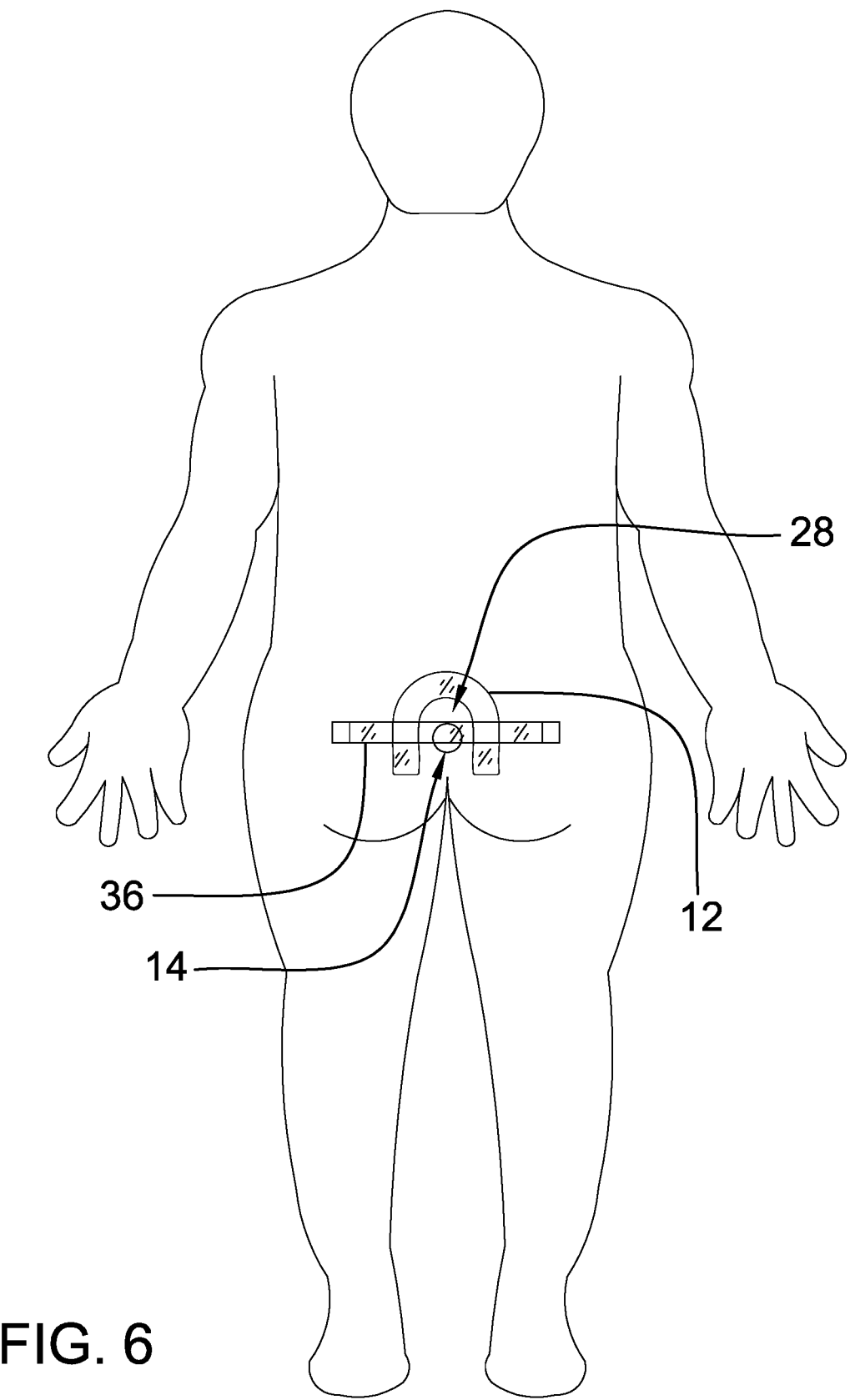
FIG. 6 is a perspective in-use view of an embodiment of the disclosure.
Figure 7:
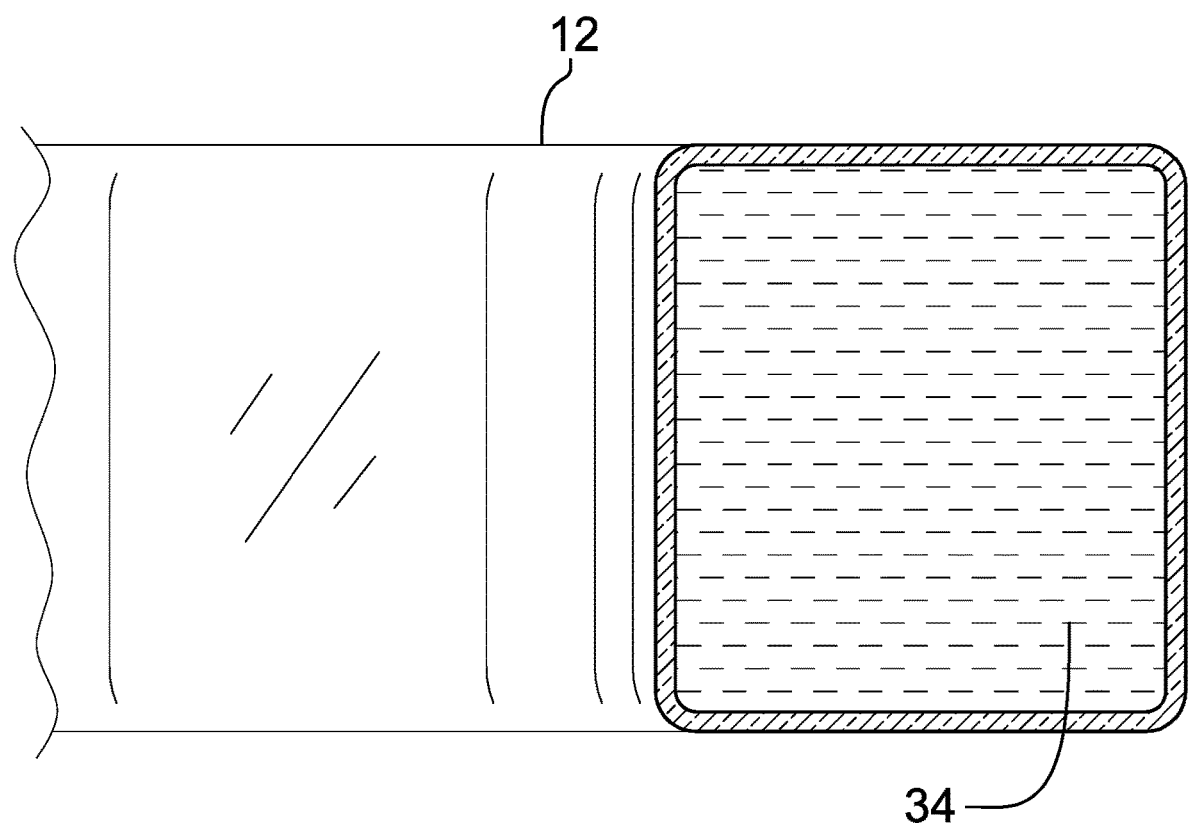
FIG. 7 is a cross sectional view taken along line 7-7 of FIG. 2 of an embodiment of the disclosure.

With reference now to the drawings, and in particular to FIGS. 1 through 7 thereof, a new dressing device embodying the principles and concepts of an embodiment of the disclosure and generally designated by the reference numeral 10 will be described.

As best illustrated in FIGS. 1 through 7, the pressure ulcer dressing assembly 10 generally comprises a cushion 12 is hollow. The cushion 12 is comprised of a fluid impermeable material, including but not being limited to, vinyl, silicone or other similar material. Additionally, the cushion 12 is comprised of a deformable material. The cushion 12 is curved such that the cushion 12 has a C shape. The cushion 12 is positionable around a pressure ulcer 14 on a patient having the cushion 12 partially encircling the pressure ulcer 14.

The cushion 12 has a first end 16, a second end 18 and an outer wall 20 extending therebetween. The outer wall 20 has a curved portion 22 that is centrally positioned a first straight portion 24 and a second straight portion 26. The first straight portion 24 extends between the first end 16 and the curved portion 22. The second straight portion 26 extends between the second end 18 and the curved portion 22. The first end 16 is spaced from the second end 18 to define an ulcer space 28 between each of the first straight portion 24 and the second straight portion 26. Additionally, the outer wall 20 has a top side 30 and a bottom side 32, and the bottom side 32 rests against the patient's skin when the cushion 12 is positioned on the patient having the pressure ulcer 14 being positioned in the ulcer space 28.

A gel 34 is provided and the gel 34 fills the cushion 12. The gel 34 absorbs weight of the patient when the cushion 12 is positioned on the patient. In this way the cushion 12 inhibits the pressure ulcer 14 from being exposed to pressure thereby enhancing healing the pressure ulcer 14. The gel 34 may comprise silicone gel or other medical grade gel that is non-toxic to human skin.

A dressing 36 is provided and the dressing 36 is coupled to the cushion 12. The dressing 36 extends laterally across the cushion 12 and the dressing 36 covers the pressure ulcer 14 when the cushion 12 is positioned on the patient. The dressing 36 has a primary end 38, a secondary end 40 and an outer surface 42 extending therebetween, and the dressing 36 is elongated between the primary end 38 and the secondary end 40. The dressing 36 may comprise a medical dressing 36 that is commonly used to treat pressure ulcers.

The outer surface 42 has an upper side 44 and a lower side 46, and the upper side 44 is bonded to the bottom side 32 of the outer wall 20 of the cushion 12. The dressing 36 extends across each of the first straight portion 24 and the second straight portion 26 of the outer wall 20 of the cushion 12. Moreover, the dressing 36 extends across the ulcer space 28 in the cushion 12. The primary end 38 is spaced from the first straight portion 24 and the secondary end 40 is spaced from the second straight portion 26.

A pair of adhesive pads 48 is provided and each of the adhesive pads 48 is coupled to the dressing 36. Each of the adhesive pads 48 adheres to the patient's skin when the dressing 36 is positioned over the pressure ulcer 14. In this way the dressing 36 and the cushion 12 are each retained on the patient. Each of the adhesive pads 48 is positioned on the lower side 46 of the outer surface 42 of the dressing 36 and each of the adhesive pads 48 is positioned adjacent to a respective one of the primary end 38 and the secondary end 40 of the dressing 36. Additionally, each of the adhesive pads 48 may comprise a medical grade adhesive that can be left on human skin for at least 5.0 consecutive days.

In use, the dressing 36 is stretched tightly across the patient's skin such that the dressing 36 covers the pressure ulcer 14. Each of the adhesive pads 48 is adhered to the patient's skin to retain the dressing 36 over the pressure ulcer 14. Additionally, the dressing 36 is oriented to facilitate the pressure ulcer 14 to be positioned in the ulcer space 28 in the cushion 12. In this way the cushion 12 partially encircles the pressure ulcer 14. Additionally, the gel 34 in the cushion 12 absorbs the weight of the patient when the patient lies on the cushion 12. In this way the cushion 12 inhibits the pressure ulcer 14 from being exposed to pressure, thereby enhancing the healing process of the pressure ulcer 14.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A pressure ulcer dressing assembly being configured to inhibit pressure from being put on a pressure ulcer, said assembly comprising:
    a cushion being hollow, said cushion being comprised of a fluid impermeable material, said cushion being comprised of a deformable material, said cushion being curved such that said cushion has a C shape, said cushion being positionable around a pressure ulcer on a patient having said cushion partially encircling the pressure ulcer;
    a gel filling said cushion, said gel configured to absorb weight of the patient when said cushion is positioned on the patient, wherein said cushion is configured to inhibit the pressure ulcer from being exposed to pressure thereby enhancing healing the pressure ulcer;
    a dressing having an inner surface coupled to said cushion and an outer surface opposite the inner surface, said dressing extending laterally across said cushion, said dressing configured to cover the pressure ulcer when said cushion is positioned on the patient; and
    a pair of adhesive pads, each of said pair of adhesive pads being coupled to the outer surface of said dressing, each of said pair of adhesive pads configured to adhere to the patient's skin when said dressing is positioned over the pressure ulcer for retaining said dressing and said cushion on the patient,
    wherein said cushion has a first end, a second end and an outer wall extending therebetween, said outer wall having a curved portion being centrally positioned a first straight portion and a second straight portion, said first straight portion extending between said first end and said curved portion, said second straight portion extending between said second end and said curved portion.

2. The assembly according to claim 1, wherein said first end is spaced from said second end to define an ulcer space between each of said first straight portion and said second straight portion.

3. The assembly according to claim 2, wherein said outer wall has a top side and a bottom side, said bottom side configured to rest against the patient's skin when said cushion is positioned on the patient having the pressure ulcer being positioned in said ulcer space.

4. The assembly according to claim 3, wherein said dressing has a primary end, a secondary end, and the outer surface extending therebetween, said dressing being elongated between said primary end and said secondary end, said outer surface having an upper side and a lower side, said upper side being bonded to said bottom side of said outer wall of said cushion having said dressing extending across each of said first straight portion and said second straight portion of said outer wall of said cushion.

5. The assembly according to claim 4, wherein said dressing extends across said ulcer space in said cushion, said primary end being spaced from said first straight portion, said secondary end being spaced from said second straight portion.

6. The assembly according to claim 4, wherein each of said adhesive pads is positioned on said lower surface of said dressing, each of said adhesive pads being positioned adjacent to a respective one of said primary end and said secondary end of said dressing.

7. A pressure ulcer dressing assembly being configured to inhibit pressure from being put on a pressure ulcer, said assembly comprising:

a cushion being hollow, said cushion being comprised of a fluid impermeable material, said cushion being comprised of a deformable material, said cushion being curved such that said cushion has a C shape, said cushion being positionable around a pressure ulcer on a patient having said cushion partially encircling the pressure ulcer, said cushion having a first end, a second end and an outer wall extending therebetween, said outer wall having a curved portion being centrally positioned a first straight portion and a second straight portion, said first straight portion extending between said first end and said curved portion, said second straight portion extending between said second end and said curved portion, said first end being spaced from said second end to define an ulcer space between each of said first straight portion and said second straight portion, said outer wall having a top side and a bottom side, said bottom side configured to rest against the patient's skin when said cushion is positioned on the patient having the pressure ulcer being positioned in said ulcer space;

a gel filling said cushion, said gel configured to absorb weight of the patient when said cushion is positioned on the patient, wherein said cushion is configured to inhibit the pressure ulcer from being exposed to pressure thereby enhancing healing the pressure ulcer;

a dressing having an inner surface coupled to said cushion and an outer surface opposite the inner surface, said dressing extending laterally across said cushion, wherein said dressing is configured to cover the pressure ulcer when said cushion is positioned on the patient, said dressing having a primary end, a secondary end, and an outer surface extending therebetween, said dressing being elongated between said primary end and said secondary end, said outer surface having an upper side and a lower side, said upper side being bonded to said bottom side of said outer wall of said cushion having said dressing extending across each of said first straight portion and said second straight portion of said outer wall of said cushion, said dressing extending across said ulcer space in said cushion, said primary end being spaced from said first straight portion, said secondary end being spaced from said second straight portion; and a pair of adhesive pads, each of said pair of adhesive pads being coupled to the outer surface of said dressing, wherein each of said pair of adhesive pads is configured to adhere to the patient's skin when said dressing is positioned over the pressure ulcer for retaining said dressing and said cushion on the patient, each of said adhesive pads being positioned on said lower surface of said dressing, each of said adhesive pads being positioned adjacent to a respective one of said primary end and said secondary end of said dressing.

* * * * *